United States Patent
McDonogh

(10) Patent No.: US 12,338,338 B2
(45) Date of Patent: Jun. 24, 2025

(54) MICROPOROUS MATERIAL AND SYSTEMS AND METHODS FOR MAKING THE SAME

(71) Applicant: Richard McDonogh, Sanford, NC (US)

(72) Inventor: Richard McDonogh, Sanford, NC (US)

( * ) Notice: Subject to any disclaimer, the term of this patent is extended or adjusted under 35 U.S.C. 154(b) by 1286 days.

(21) Appl. No.: 16/631,803

(22) PCT Filed: Jul. 19, 2018

(86) PCT No.: PCT/US2018/042789
§ 371 (c)(1),
(2) Date: Jan. 16, 2020

(87) PCT Pub. No.: WO2019/018587
PCT Pub. Date: Jan. 24, 2019

(65) Prior Publication Data
US 2020/0172694 A1    Jun. 4, 2020

Related U.S. Application Data

(60) Provisional application No. 62/534,387, filed on Jul. 19, 2017.

(51) Int. Cl.
*C08J 9/28* (2006.01)
*A61M 5/14* (2006.01)
(Continued)

(52) U.S. Cl.
CPC ........... *C08J 9/28* (2013.01); *A61M 5/165* (2013.01); *B01D 67/0006* (2013.01); *B01D 67/00135* (2022.08); *B01D 67/00165* (2022.08); *B01D 67/0095* (2013.01); *B01D 69/02* (2013.01); *B01D 71/441* (2022.08); *B01D 71/5211* (2022.08); *B01D 71/5222* (2022.08);
(Continued)

(58) Field of Classification Search
CPC .......... C08J 9/28; C08J 2201/0422; C08J 2205/022; C08J 2205/044; C08J 2207/10; C08J 2339/06; C08J 2381/06; A61M 5/165; A61M 2005/1657; B01D 67/0006; B01D 67/0013; B01D 67/0016; B01D 67/0095; B01D 2323/30; B01D 71/44; B01D 71/68; B01D 69/02
See application file for complete search history.

(56) References Cited

U.S. PATENT DOCUMENTS

| 5,250,028 A | 10/1993 | Theeuwes et al. |
| 2002/0162792 A1 | 11/2002 | Zepf |

(Continued)

FOREIGN PATENT DOCUMENTS

| CN | 1585627 A | 2/2005 |
| CN | 103463712 A | 9/2013 |

(Continued)

OTHER PUBLICATIONS

Richard et al., "Pressure-driven molecular dynamics simulations of water transport through a hydrophilic nanochannel," Molecular Physics, Apr. 11, 2016, 114:18, 2655-2663.

(Continued)

*Primary Examiner* — Youngsul Jeong
(74) *Attorney, Agent, or Firm* — Hunt IP Law

(57) ABSTRACT

The invention disclosed herein generally relates to matrices comprising polymers and methods for preparing them.

10 Claims, 11 Drawing Sheets

(51) Int. Cl.
*A61M 5/165* (2006.01)
*B01D 67/00* (2006.01)
*B01D 69/02* (2006.01)
*B01D 71/44* (2006.01)
*B01D 71/52* (2006.01)
*B01D 71/68* (2006.01)

(52) U.S. Cl.
CPC ..... *B01D 71/68* (2013.01); *A61M 2005/1657* (2013.01); *B01D 2323/30* (2013.01); *B01D 2325/341* (2022.08); *C08J 2201/0422* (2013.01); *C08J 2205/022* (2013.01); *C08J 2205/044* (2013.01); *C08J 2207/10* (2013.01); *C08J 2339/06* (2013.01); *C08J 2381/06* (2013.01)

(56) References Cited

U.S. PATENT DOCUMENTS

| | | |
|---|---|---|
| 2003/0064095 A1 | 4/2003 | Martin et al. |
| 2004/0168974 A1 | 9/2004 | Hughes et al. |
| 2011/0233138 A1* | 9/2011 | Kyu ..................... C07D 311/86 549/392 |
| 2016/0213861 A1* | 7/2016 | Whitaker ............. A61M 5/1411 |

FOREIGN PATENT DOCUMENTS

| | | |
|---|---|---|
| WO | 9009200 A1 | 8/1990 |
| WO | 2002005937 A2 | 1/2002 |
| WO | 2006131290 A1 | 12/2006 |
| WO | 2010059327 A2 | 5/2010 |

OTHER PUBLICATIONS

Jin et al., "Understanding flow enhancement in graphene-coated nanochannels," Electrophoresis, 2019, 40, 859-864.

Wu et al., "Wettability effect of nanoconfined water flow," PNAS, Mar. 13, 2017, 114(13), 3358-3363.

McKinnon, Lani Paige, "High-Pressure Flow Enhancement of Nanoconfined Fluids through Novel Hydrophilic Silica Nanofluidic Devices," The University of Utah ProQuest Dissertations Publishing, 2022, 30000833.

* cited by examiner 0.1 μm commerical membrane, 0.2 μm commerical membrane 0.6 MPa bubble point membrane of the invention 0.4 MPa bubble point membrane of the invention Caster Drum Drier Staged rinse, residence time 5 minutes                Edge Aligned wind up

MICROPOROUS MATERIAL AND SYSTEMS AND METHODS FOR MAKING THE SAME

CROSS-REFERENCE TO RELATED APPLICATION

The present application is a U.S. National Stage entry under U.S.C. 371 of International Application No. PCT/US2018/042789, filed on Jul. 19, 2018, designating the United States of America and published in English on Jan. 24, 2019, which in turn claims priority to U.S. Provisional Application No. 62/534,387, filed Jul. 19, 2017. The entire contents of each of the foregoing is hereby incorporated by reference herein.

FIELD OF THE INVENTION

The invention disclosed herein generally relates to matrices comprising polymers and methods for preparing them.

BACKGROUND

Polymeric matrices, including porous matrices and membrane matrices, are used in a variety of filtration applications, such as purification and testing in the food and beverage industry, water treatment, pharmaceuticals, and in medical laboratories.

Most polymeric matrices are generally made by first preparing a casting solution, or dope, made up of the chosen polymer in a suitable solvent. The casting dope is then formed into a thin film and the polymer is precipitated or coagulated into a solid phase. Precipitating or coagulating the polymer into a solid porous matrix or membrane matrix is normally carried out by evaporating the solvent or contacting the polymer with a non-solvent liquid in a coagulation bath. By varying the composition of the polymer or casting solution, or the process conditions, matrices having varying morphology, porosity, and performance characteristics are produced.

SUMMARY OF THE INVENTION

Figure 1:
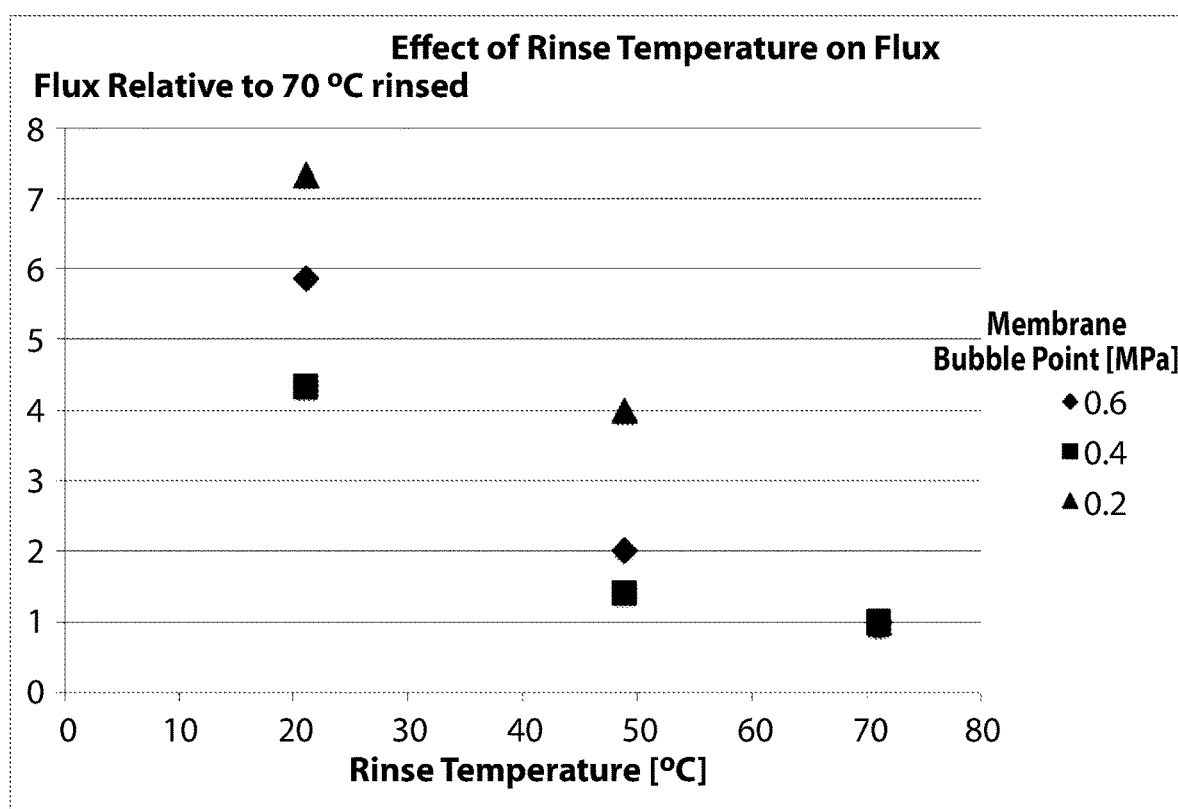
FIG. 1 depicts results from experiments testing the effect of rinse temperature on the matrix.

Embodiments of the invention relate to a matrix that can be capable of passage of water therethrough having a flow rate at a temperature such as 20° C. that meets or exceeds a flow value produced by application of Formula 1. Some embodiments of the invention relate to a matrix that can be capable of passage of water therethrough having a flow rate at 20° C. that meets or exceeds a flow value produced by application of Formula 1:

$$\text{Flow} = k \cdot (Bp - b_0)^L \quad \text{Formula 1:}$$

where when the bubble point with water at 20° C. is between 0.01 and 0.25 MPa, $k=31026$, $L=-1.00$, and $b_0=0.01034$; and bubble point with water at 20° C. is greater than 0.25 MPa, $k=5797$, $L=-1.35$, and $b_0=0.1379$. In this formula, flow is expressed in L/m2/h, the pressure can be at 1 bar. The embodiment described in this formula is for membranes of thickness in the range of approximately 100-140 micrometers.

The membrane can have flow properties which makes it useful in flow settings. For example, the matrix can further be capable of full flow-stop performance at a drop distance of at least 1 meter. In some embodiments, the drop distance can be at least 1.5 meters.

In some embodiments, the matrix can be capable of passage of 23° C. water therethrough at a rate of at least 120 ml/minute through a matrix area of about 0.785 cm$^2$ (diameter 1 cm). In some embodiments, the rate of water therethrough can be at least 145 ml/minute. In some embodiments, the rate of water therethrough can be up to over 200 ml/min. In some embodiments, the matrix area is about 3 cm$^2$.

In some embodiments, the matrix can have a composition including at least one substantially non-sulfonated polymer and at least one compatible polymer. The at least one compatible polymer can be compatible with the at least one substantially non-sulfonated polymer. In some embodiments, the composition can include at least two substantially non-sulfonated polymers. In some embodiments, the composition can include at least two compatible polymers. In some embodiments, the composition can include polymers of the same type but of different molecular weight grade.

In some embodiments, the compatible polymer includes a sulfone polymer. In some embodiments, the sulfone polymer can include polyethersulfone (PES), polysulfone (PSU), and/or the like.

In some embodiments, the substantially non-sulfonated polymer includes polyvinylpyrrolidone (PVP), and/or the like. In some embodiments, the PVP has a molecular weight less than 2800 kDa. In some embodiments, the PVP has a molecular weight between 3 kDa and 2800 kDa.

In some embodiments, the water can be replaced with another liquid. The liquid can be deionized water, or the like. The liquid can also be an isotonic salt solution, a sugar solution, a liquid fat solution, or the like.

Some embodiments of the invention relate to an IV device including the matrix. The IV device can be capable of passage of water therethrough at a rate of at least 120 ml/minute, and can be further capable of full flow-stop performance at a drop distance of at least 1 meter. In some embodiments, the drop distance can be at least 1.5. meters. In some embodiments, the rate of water therethrough can be at least 140 ml/minute. In some embodiments, the rate of water therethrough can be up to over 200 ml/min.

Some embodiments of the invention relate to a method of producing a porous, hydrogel matrix. The method can include (1) providing a dope mix including at least one matrix polymer and at least one non-solvent polymer; (2) producing a first cast material by casting the dope mix in a form such as a thin layer, a continuous sheet, a hollow fiber, a tube, a coating on a monolith, or the like; (3) exposing the first cast material for a predetermined period of time to a humid gas or humid mix of gases to produce a second cast material; (4) forming the porous matrix by immersing the second cast material in a coagulation bath including a quenching solution that includes at least one non-solvent; (5) rinsing the matrix in a rinse bath to perform pre-drying rinse, such that between 1% and 15% of the original non-solvent polymer remains in contact with the matrix after rinsing; and (6) drying the matrix to form a porous hydrogel matrix with which the non-solvent polymer is substantially bound.

In some embodiments, the non-solvent polymer can be PEG. Alternatively, water can be used. Alternatively, a combination of PEG and water can be used.

In some embodiments, the drying temperature is sufficient to raise the temperature of the matrix material to at least 95% of the glass transition temperature (Tg) of at least one of the polymers of which the matrix is comprised.

In some embodiments, the matrix material includes at least two components: a first component having a lower Tg and a second component having a higher Tg. In some embodiments, the temperature of the matrix material is raised to at least 95% of the lower Tg, or at least 95% of the higher Tg, or at least 95% of the average of the higher and lower Tg, or at least 95 of the average of all Tg of all components of the matrix material having a Tg. In some embodiments, the temperature of the matrix material is raised to 96%, 97%, 98%, or 99% of the Tg, either the Tg of the single component having a Tg, or the lower Tg of the two or more components having a Tg, or the average Tg of the two or more components having a Tg, or the higher Tg of the two or more components having a Tg. In still other embodiments, the temperature of the matrix material is raised to 70%, 75%, 80%, 85%, 90%, 91%, 92%, 93% or 94% of the relevant Tg, wherein relevant Tg is selected from any of the approaches to choosing a Tg as described in this paragraph.

In some embodiments, a post-drying rinse can release less than 90 percent of the remaining non-solvent polymer from the matrix.

In some embodiments, cross-linking between the non-solvent polymer and the matrix polymer can exist in the dried membrane. In some embodiments, the cross-linking is reversible. In some embodiments, the cross-linking is permanent.

In some embodiments, the non-solvent polymer can include polyethylene glycol (PEG) and the matrix polymer can include a substantially non-sulfonated polymer and a compatible polymer. The compatible polymer is compatible with the substantially non-sulfonated polymer. In some embodiments, caprolactam or caprolactam-like compounds can be used in addition to PEG or instead of PEG.

In some embodiments, the compatible polymer can include a sulfone polymer. In some embodiments, the sulfone polymer can include polyethersulfone (PES).

In some embodiments, the substantially non-sulfonated polymer can include polyvinylpyrrolidone (PVP). In some embodiments, the PVP has a molecular weight less than 2800 kDa. In some embodiments, the coagulation can be conducted at a temperature between 3° C. and 95° C.

In some embodiments, the pre-drying rinse can be conducted at a temperature between 3° C. and 95° C. In some embodiments, the pre-drying is conducted using a rinsing solution comprising water.

In some embodiments, the non-solvent of the coagulation bath can include water or PEG or a combination thereof.

In some embodiments, the coagulation bath further includes a solvent, a non-solvent, a non-solvent polymer, a surfactant, a salt, and/or any combination thereof.

In some embodiments, the solvent of the quenching solution includes NMP, and/or DMSO, and/or DMAC.

In some embodiments, the matrix can have a relationship of flow rate to bubble point that meets or exceeds a flow value produced by application of Formula 1

$$\text{Flow} = k \cdot (Bp - b_0)^L \qquad \text{Formula 1:}$$

where when the bubble point with water at 20° C. is between 0.01 and 0.25 MPa, k=31026, L=−1.00, and $b_0$=0.01034; and bubble point with water at 20° C. is greater than 0.25 MPa, k=5797, L=−1.35, and $b_0$=0.1379. In this formula, flow is expressed in L/m2/h, the pressure can be at 1 bar. The embodiment described in this formula is for membranes of thickness in the range of approximately 100-140 micrometers.

In some embodiments, the membrane can be dried under longitudinal tension of 20 N/m width. In some embodiments, the membrane can be dried at or about 5, 10, or 15 N/m, or at about 25, 30, 35, 40, 45, 50, or more N/m, depending upon the composition of the membrane, and the desired structural and performance properties of the final membrane product.

Some embodiments of the invention relate to a filtration matrix having a flow rate at a temperature such as 20° C. that meets or exceeds a flow value produced by application of Formula 1

$$\text{Flow} = k \cdot (Bp - b_0)^L \qquad \text{Formula 1:}$$

where when the bubble point with water at 20° C. is between 0.01 and 0.25 MPa, k=31026, L=−1.00, and $b_0$=0.01034; and bubble point with water at 20° C. is greater than 0.25 MPa, k=5797, L=−1.35, and $b_0$=0.1379. In this formula, flow is expressed in L/m2/h, the pressure can be at 1 bar. The embodiment described in this formula is for membranes of thickness in the range of approximately 100-140 micrometers.

Some embodiments relate to a method of producing a porous, hydrogel matrix material. The method can include providing a dope mix comprising at least one matrix polymer and at least one non-solvent polymer; producing a first cast material by casting the dope mix in a form selected from a thin layer, a continuous sheet, a hollow fiber, a tube, a coating on a porous substrate, a coating on a non-porous substrate, a coating on a monolith, and/or the like, and/or combinations thereof; exposing the first cast material for a predetermined period of time to a humid gas or humid mix of gases to produce a second cast material; forming the porous matrix by immersing the second cast material in a coagulation bath comprising a quenching solution, the quenching solution comprising at least one non-solvent; rinsing the porous matrix in a rinse bath to perform a pre-drying rinse, such that between 1% and 15% of the original non-solvent polymer remains in contact with the porous matrix after rinsing; and drying the porous matrix to form a porous hydrogel matrix material with which the non-solvent polymer is substantially bound.

In some embodiments, the drying temperature can be sufficient to raise the temperature of the porous hydrogel matrix material to at least 95% of Tg of at least one of the polymers of which the porous matrix is comprised.

In some embodiments, the porous hydrogel matrix material can include at least two components, a first component having a lower Tg and a second component having a higher Tg, and wherein the temperature of the matrix material is raised to at least 95% of the lower Tg, or at least 95% of the higher Tg, or at least 95% of the average of the higher and lower Tg, or at least 95 of the average of all Tg of all components of the matrix material having a Tg.

In some embodiments, in a post-drying rinse, less than 50 percent of the remaining non-solvent polymer can be released from the matrix.

In some embodiments, cross-linking can be between the non-solvent polymer and the matrix polymer exists in the dried membrane.

In some embodiments, the cross-linking can be reversible.

In some embodiments, the non-solvent polymer can include polyethylene glycol (PEG). In some embodiments, the matrix polymer can include a substantially non-sulfonatable polymer and a compatible polymer, wherein the compatible polymer can be compatible with the substantially non-sulfonatable polymer.

In some embodiments, the coagulation can be conducted at a temperature between 3° C. and 95° C.

In some embodiments, the pre-drying can be conducted using a rinsing solution comprising water.

In some embodiments, the non-solvent of the coagulation bath can include water or PEG or a combination thereof. In some embodiments, the coagulation bath can further include at least one of: a solvent, a non-solvent, a non-solvent polymer, a surfactant, a salt, or any combination thereof.

In some embodiments, the solvent of the quenching solution can include NMP, DMSO, DMAC, or the like, or combinations thereof.

In some embodiments, the porous matrix can have a relationship of flow rate to bubble point that meets or exceeds a flow value produced by application of Formula 1:

$$\text{Flow}=k \cdot (Bp-b_o)^L;\qquad \text{Formula 1:}$$

wherein when bubble point with water at 20° C. is between 0.01 and 0.25 MPa, k=31026, L=−1.0, and $b_o$=0.01034; and wherein when bubble point with water at 20° C. is greater than 0.25 MPa, k=5797, L=−1.35, and $b_o$=0.1379; and wherein flow is expressed in L/m²/h.

In some embodiments, the porous matrix can have a flow rate at 23° C. that meets or exceeds a flow value produced by application of Formula 1

$$\text{Flow}=k \cdot (Bp-b_o)^L;\qquad \text{Formula 1:}$$

wherein when bubble point with water at 20° C. is between 0.01 and 0.25 MPa, k=31026, L=−1.0, and $b_o$=0.01034; and wherein when bubble point with water at 20° C. is greater than 0.25 MPa, k=5797, L=−1.35, and $b_o$=0.1379; and wherein flow is expressed in L/m²/h.

In some embodiments, the porous matrix can have a composition including at least one substantially non-sulfonatable polymer and a compatible polymer, wherein the compatible polymer can be compatible with the substantially non-sulfonatable polymer.

In some embodiments, the compatible polymer can include a sulfone polymer and the sulfone polymer can include polyethersulfone (PES).

In some embodiments, the substantially non-sulfonatable polymer can include polyvinylpyrrolidone (PVP) with a molecular weight less than 2800 kDa.

In some embodiments, the porous matrix can be a flow-stop matrix capable of passage of water therethrough at a rate of at least 120 ml/minute through a matrix area of 3 cm², and further capable of full flow-stop performance at a drop distance of at least 1 meter.

DETAILED DESCRIPTION OF THE INVENTION

Introduction

Using appropriate solvents, polymers can be dissolved to make dopes of polymers. The polymers can be mixtures of different polymers. By casting these dopes in coagulation baths of different compositions, porous matrices of polymers or mixtures of these with other polymers can be produced directly. These matrices, defined as materials having a polymer phase and a void phase, have a range of structures depending on the composition of the dope and the coagulation bath. These structures include closed cells, open cells with a gradation of pores from one side to the other (gradation includes from small to very large), or finger-type structures (controlled macrovoids). In some embodiments, one surface of these matrices can have no pores (when viewed by SEM), or it can have pores up to 20 μm or more in size. The other surface can have pores of similar size or larger. These matrices can be hydrophilic, and can be permeable or nonpermeable. The matrices can also be non-hydrophilic, e.g. being of a composition that includes a significant amount of PVDF, even when casting into water.

Structurally, the matrices appear to have an hourglass configuration in cross-section and, at the level of structure visible in SEM, appear very similar or essentially identical in structure to Membrana membranes (Membrana GmbH/3M). Membrana membranes are typical in the market of flat sheet membranes. FIG. 7 shows SEM images of Membrana membranes 0.1 μm (a) and 0.2 μm (b), and current membrane 0.6 MPa (c) and 0.4 MPa (d). That is, the apparent channel size of the membrane appears to be much smaller in the middle and more open at the top and bottom, with the neck varying in depth with the pore size, when viewed in cross-section. However, at a submicroscopic level (below the resolution of SEM), the structure and surface chemistry of the matrix is different from the Membrana membrane as demonstrated by the extremely different performance of the matrices as compared with the Membrana membrane.

The Matrix Polymer

In some embodiments of the invention, the matrix polymer can include a substantially non-sulfonated polymer and a compatible polymer, wherein the compatible polymer is compatible with the substantially non-sulfonated polymer. In this context, "substantially nonsulfonated" means that sulfonation is not a significant outcome in standard chemical reactions under generally-employed conditions, although sulfonation to some degree can be obtainable under extreme conditions and/or with low efficiency.

Examples of substantially non-sulfonated polymers can include non-aryl polysulfone, non-aryl polyethersulfone, Kevlar™, polyetherketone, PVDF, esters of cellulose, polyvinylpyrrolidone (PVP K value (intrinsic viscosity) 10 up to K value 360, available from Sigma Aldrich), polyethylene glycol (100 to 400 molecular weight, or greater), or the like. If polyvinylpyrrolidone is used, a more open matrix structure is generated. Such substantially non-sulfonated polymers can form up to 100% of the polymer in the mixture.

In general, at higher concentrations of the non-sulfonated polymer in the casting solution, more open structures, or finger structures, are produced. At lower concentrations of non-sulfonated polymer, more closed structures, or cell structures, can be produced. At high solid content, fingers voids are formed, there is a skin and the membrane is not so open. In general, the ratios of the polymer with respect to the other ingredients affects the final structure.

Examples of compatible polymers include a sulfone polymer, or the like. Suitable aryl sulfonates can include polyethersulfone (available from BASF under the trade name "Ultrason E", Varadel from Solvay) and polysulfone (available from BASF under the trade name "Ultrason S", Udel from Solvay). Other suitable aryl sulfonate polymers that can be used include polyarylene etherethersulfone, polyarylene ethersulfone, polyarylenepropylenearylene etherether sulfone, polyaryl sulfones, polyaryl ether sulfones, polyaryl ether ketones, poly ether ether ketones, polystyrene, polyphenylsulfone, copolymers of such, and the like.

The Solvent

Determination of the appropriate solvent and its relative content in the composition from which the matrices are cast is driven by the polymers chosen for use, and is within the level of skill in the art.

Additional Additives

Other additives typically used in membrane production can also be used. Non-limiting examples of such additives include alcohols (such as ethanol), acid non-degrading organic solvents (such as polar solvents), and alkali metal halides (such as NaCl and LiCl). Non-solvents (for the polymers) can also be added. In general, when higher concentrations of non-solvent are used, a more open structure and a less dense skin are produced. Lower concentrations result in more closed structures and denser skin. Up to about 10 g/l of solid additives and up to about 10 wt. % liquid additives are typically added to the polymer dopes. However, depending upon the additive and other components present in the polymer dope, higher additive levels can be suitable.

Preparation of Polymer Dopes

Polymer dopes can be prepared by dissolving one or more polymers and, optionally, one or more additives in a solvent, then casting the resulting solution to produce a cast material in a form such as a thin layer, a continuous sheet, a hollow fiber, a tube, a coating on a porous substrate, a coating on a non-porous substrate, a coating on a monolith, or the like.

The polymer dope mix can comprise at least one matrix polymer and at least one non-solvent polymer. The non-solvent polymer can be miscible in the solvent and/or in one or both of the matrix polymers as well as in the coagulation bath. For example, the non-solvent polymer can be PEG.

After the polymer(s) and optional additives are mixed together, the solvent can be added. For example, 99 parts by weight to 55 parts by weight of the solvent, in concentrated form, can be used to dissolve 1 to 45 parts by weight of polymer. Alternatively, 95 to 75 of the solvent, in concentrated form, can be used to dissolve 5 to 55 parts by weight of polymer. If the solvent is in diluted form, additional solvent can be required to dissolve the same quantity of polymer. Preferably, the mixing is conducted at room temperature.

The mixture of polymer(s) and optional additives can be heated to a temperature of from 25° C. to 95° C. in many cases to a temperature of about 75° C., plus or minus about 2 or 5 or 10 degrees, or more. The mixture can be then mixed, e.g., in a ball mill, until the polymer is substantially dissolved or dispersed. Typically, about 4 to 12 hours is needed for dissolution. Actual temperature and shear of mixing may affect the time to achieve substantial dissolution or dispersion.

Preparation of Matrices from Polymer Dopes

The polymer dopes as described above can be cast into porous matrices, non-porous matrices or membrane matrices using any conventional procedure wherein the casting solution is formed into a thin wet film, as in spreading as a layer onto a nonporous support from which the matrix later can be separated after coagulating. The matrices can be cast manually by being poured, cast, or spread by hand onto a casting surface followed by application of a coagulation liquid onto the casting surface. Alternatively, the matrices can be cast automatically by pouring or otherwise casting the solution onto a moving bed. For example, the bed can move between about 0.15 meters per minute and about 15 meters per minute. The temperature of the polymer dope at casting can affect the structure of the resulting membrane.

One type of moving belt support is polyethylene coated paper. In casting, particularly in automatic casting, mechanical spreaders can be used. Mechanical spreaders include spreading knives, a doctor blade or spray/pressurized systems, or the like. An example of a spreading device can be an extrusion die or slot coater which has a chamber into which the casting formulation can be introduced. The casting solution is then forced out of the chamber under pressure through a narrow slot. Matrices can also be cast by means of a doctor blade with a knife gap of typically about 300 microns to 800 microns, for example, about 500 microns. The relationship between the knife gap at casting and the final thickness of the matrix is a function of the composition and temperature of the casting solution, the duration of exposure to the gaseous environment, such as humid air, the relative humidity of the air during exposure. In addition, the temperature of the coagulation bath and many other factors can affect the overall thickness of the final matrix. Matrices typically shrink upon coagulation or gelling, losing from about 20% to about 80% of their thickness. Casting solution temperatures of between about 20° C. and 80° C. are typically utilized. In some embodiments, casting can be advantageously performed at 25, 30, 35, 40, 45, 50, 55, 60, 65, 70, 75, 85, or 90 degrees C., depending upon the composition, the desired membrane structure and performance, and other factors affecting membrane structure and performance.

Generally, to produce an open cell membrane matrix, the cast material is exposed to a gaseous environment, such as air, sufficiently long to induce formation of relatively large surface pores. The gaseous environment can also be a mixture of gases. Examples of gases include nitrogen steam mixtures or the like. Exposure time and exposure conditions that exist between casting and coagulating the casting solution are factors that can affect pore formation. In one embodiment, the casting solution can be exposed to humid air after casting but before coagulation. Relative air humidity can be greater than about 60%. However, ambient humidity conditions and relative air humidities less than or equal to about 60% are also acceptable. In addition, the air is preferably circulated to enhance contact with the cast solution. If no air is used and cast into a tank of high solvent content, it is possible to generate structure without the aid of humid air. In some cases, depending upon other factors including the polymer, the solvent, and the quenching temperature and solution, as well as other factors, the acceptability humidity at casting can be higher than 60%.

The exposure time to air can be from about 0.1 seconds to about 5 minutes. Exposure time can depend on the speed of the moving bed. Increasing the air exposure time, over this range, tends to increase permeability of the resulting membrane. In one embodiment, the air exposure time is 3 to 10 seconds. In some cases, exposure to the air can be unnecessary for pore formation.

Following casting and exposure to a gaseous environment, such as air, the cast solution is coagulated. In one embodiment, coagulation can be accomplished by transporting the cast matrix on a moving belt into the coagulation liquid, or extruding as an unsupported hollow tube. In the coagulation bath, the polymer coagulates to produce a matrix having the requisite pore and surface structure. The coagulation bath can include a quenching solution. The quenching solution can include at least one non-solvent. For example, the non-solvent can be water, PEG or mixtures of the two. The coagulation bath can further include a solvent, a non-solvent, a non-solvent polymer, a surfactant, a salt, and a caprolactam, and/or any combination thereof. The solvent can include NMP, DMSO, DMAC, and/or the like.

The temperature of the coagulation bath can affect the porosity of the matrix. In general, warmer coagulation baths result in more porous matrices. When colder temperatures are used, a tighter surface and a more regular under-structure is produced, regardless of the resulting structure type, e.g., regular fingers or regular cells are produced. Generally, a wide temperature range can be utilized in the coagulation step, ranging from about 0° C. to 90° C. In some embodiments, the temperature can range from about 1° C. to about 60° C. The lower temperature limit is determined by the freezing point of the particular coagulation liquid. In some embodiments, the coagulation liquid is water and the coagulation temperature is between about 22° C. (or room temperature or slightly above room temperature) and about 40° C. The temperature of the coagulation bath can cause marked changes in the pore diameters of the microporous skin of the membrane and also in its internal structure. Where higher coagulation temperatures are utilized, the membranes possess both larger skin pores and enhanced asymmetry. Conversely, where lower temperatures are utilized, smaller pores form and asymmetry can be reduced. The pH of the coagulation bath can also affect coagulation time and pore size. Generally, the lower the pH of the coagulation bath, the slower the coagulation and the larger the pore size. The pH of the coagulation bath can range from 1 to 13. The pH of the coagulation bath can typically range from 1 to 8 or from 5 to 6. The pH can be adjusted by adding a suitable acid or base to the coagulation bath.

Matrices are recovered from the coagulation bath in the conventional manner involving physical removal, neutralizing, washing with deionized water and oven- or air-drying. Matrices produced by the methods described above can be up to 1000 microns thick, or more. In some embodiments, the thickness can be less than about 300 microns. For example, the thickness can be about 100 microns. It is well known that several parameters such as polymer solution viscosity, polymer solution flow rate from the casting knife, support belt speed, environmental and coagulation conditions, and the like affect the final thickness. These can all be adjusted to achieve the desired porous matrix, non-porous matrix or membrane matrix. Generally, faster coagulation results in thicker film production.

After the resulting matrix is removed from the coagulation bath, it is transferred to a different bath. The bath can contain water. The bath can also contain a basic solution in order to neutralize any remaining acid. Any suitable solution prepared by dissolving a base in a solvent can be used. For example, the solution can be aqueous sodium carbonate, for example, at a concentration of from 1 to 10 wt. % and at a pH of from 10 to 14. Neutralization can be preceded or followed by one or more rinsing steps, e.g., in a water bath. This pre-drying rinse can be conducted at a temperature between 3° C. and 95° C. For example, the temperature can be about 3° C., 10° C., 40° C., 65° C., or 95° C.

It is generally accepted that post coagulation, the nascent membrane must be rinsed to remove all remaining dope solutes from the matrix such that only the solid polymer is left before drying. This is not the case, and it is indeed important to the performance of the resultant matrix as to the way in which the nascent membrane is washed. The amount of washing can affect the flow rate and/or the bubble point of the membrane. For example, drying a membrane that has been rinsed to certain degree, but not completely, can result in a higher membrane flow rate at any given bubble point compared to a completely rinsed membrane. A washing step can also be repeated on an already dried membrane to alter flow rate. The washing step can be quantified by the amount of non-solvent polymer that is washed away. For example, the flow of a matrix produced where 95% of the initial solution's non-solvent polymer has been removed can be up to an order of magnitude higher than that of the same matrix which has had 99.5% of the initial solutions non-solvent polymer.

After rinsing and neutralization when required, the matrix or membrane is dried to expel additional increments of liquid present, e.g., solvent or coagulation liquid. If the matrix is in sheet form, it can be dried under light tension to prevent shrinkage (i.e., to limit shrinkage to less than 10%). Generally, greater shrinkage (on a percentage basis) is observed for thicker wet matrices or membranes. Drying the matrix can form a porous hydro gel matrix where some or all of the non-solvent polymer is substantially bound. The drying temperature can be sufficient to raise the temperature of the matrix material to at least 95% of Tg of at least one of the polymers of which the matrix is comprised. For example, the drying temperature can be about 150° C. For example, the drying temperature can be at or about 190° C. The drying temperature can be higher, and can depend upon the composition of the membrane.

The commonly held consensus is that once the matrix has been rinsed, it should be dried to remove all remaining volatile components, for example water from the rinse bath. A typical control parameter is the residual moisture content of the dried material. This is typically achieved based on the energy needed to remove the volatiles, and design of the drying process is based around energy input and speed of throughput. Further, in continuous system, the web controls are designed to ensure passage of the material through machines which preventing tearing and folding. It is indeed important to the performance of the resultant matrix as to the way in which the nascent membrane is dried. By optimizing the rinse to ensure an amount of the residual components such as the non-solvent polymer are present, drying the matrix can form a porous hydro gel matrix where some or all of the non-solvent polymer is substantially bound. The drying temperature can be sufficient to raise the temperature of the matrix material to at least 95% of Tg of at least one of the polymers of which the matrix is comprised. For example, the drying temperature can be about 150° C. For example, the drying temperature can be at or about 190° C. The drying temperature can be higher. When dried at such a temperature, when under optimized web tension, matrices of substantially higher performance can be produced.

In some embodiments, the matrix material can include at least two components: a first component having a lower Tg and a second component having a higher Tg, where the temperature of the matrix material is raised to at least 95% of the lower Tg, or at least 95% of the higher Tg, or at least 95% of the average of the higher and lower Tg, or at least 95 of the average of all Tg of all components of the matrix material having a Tg.

A post-drying rinse can also be included. In some embodiments, in the post-drying rinse, less than 90 percent of the remaining non-solvent polymer is released from the matrix. In some embodiments less than 50 percent of the remaining non-solvent polymer is released, such as 30, 35, 40, or 45%, or 55, 60, 65, 70, 75, 80, or 85%. The post-drying rinse can include water, a non-solvent extractant or combinations thereof or the like.

The overall properties for the porous matrices or membrane matrices of the present invention can also be varied by varying parameters such as the polymer, polymer concentration in the dope, solvent(s) and additive nature and concentration, relative degree of homogeneity or stability of the casting solution, exposure time to a gaseous environment following casting, coagulation liquid and temperature and other variables as are herein described.

Morphology and Properties of Matrices

Porous matrices, non-porous matrices and membrane matrices can be produced according to the method described above. The support region, i.e., the region between the two surfaces of the matrix, can include structures such as closed cells, isotropic flow channels having substantially constant pore size throughout the thickness of the matrix, isotropic open cells, asymmetric flow channels having increasing pore size from one surface of the matrix to the other, flow channels having pore size which change with distance from one surface of the matrix or the other, macrovoids, and/or finger structures. The internal (cross sectional) structure of the matrices can be a hourglass structure.

Crosslinking between the non-solvent polymer and the matrix polymer can exist in the membrane. The cross linking can be reversible or permanent.

The thicknesses of the matrices can range from about 5 μm to 1000 μm. For example, the thicknesses of the matrices are generally less than about 300 μm such as, for example, 250, 225, 200, 175, 150, 125, 100, or more preferably less than about 100 μm, such as, for example, 20, 35, 50, 85, or the like. In some embodiments the membranes are over 300 microns thick, including, for example, 350, 400, 450, 500, 600, 700, 800, and 900 microns thick. The matrices can have no pores, or pores ranging in size from 0.001 μm to about 100 μm, for example, 0.005, 0.01, 0.05, 0.1, 0.5, 1, 5, 10, 15 up to about 20 μm or more such as, for example, 25, 30, 40, 50, 60, 70, 80, or 90. Density of pores can range from none to 1000 pores/mm2, or more (assuming 100% porosity of 10 nm pores), such as, for example, 1, 2, 3, 10, 30, 100, 300, 500, 750, or 900. The pores can be distributed asymmetrically, randomly or in a structured manner.

The matrices described above are in the form of flat sheets. However, the matrices can be produced in other forms as well, e.g., hollow fibers, tubes, coatings on porous supports, and the like. The processes by which these other forms can be produced are well-known in the art. For example, hollow fibers can be produced by extruding the polymer dope through multiple bore spinnerets, or by coating a porous support with the polymer dope, allowing the dope to penetrate the support, then quenching the dope.

The matrices can be hydrophilic and wettable with water. Water is observed to penetrate into the matrices. The matrices can also be hydrophobic based on the choice of polymers.

Performance of Matrices

Flow value is defined by the rate at which 23° C. water flows through the matrix of an area standard in the use for flow-stop membranes in medical settings. In the present invention, the flow value of the matrices can be at least about 120, 140, 160, 180, 200 or more ml/minute. For example, the flow rate can be at least 120 ml/minute. In other examples, the flow rate can be up to over 200 ml/min. The average can be about 145 ml/min with range up to 165 ml/min.

Flow-stop performance is defined in some embodiments by drop distance: the maximum amount of drop in height between the position of a matrix connected to a vertical tube, for example, and the end of such tube, wherein the matrix is capable of stopping flow once air contacts above the matrix. A column of fluid in a tube below the matrix exerts a force upon the matrix that is proportional to the drop distance, such that fluid in a tube having a larger drop distance exerts a greater force than fluid in a tube having a shorter drop distance. Thus, a greater drop distance indicates a greater flow-stop capacity, or a greater resistance to flow when fluid above the matrix has been depleted and the matrix comes into contact with air. Accordingly, two matrices of equal area connected to tubes of equal inner diameter can be compared, in terms of their ability to stop flow up to a certain drop distance. In the present invention, the flow-stop performance can occur up to a drop distance of 0.5, 1, 1.5, 2, or more meters. For example, the flow-stop performance can occur up to a drop distance of at least 1 meter.

In some embodiments, the flow rate can meet or exceed the flow value provided by the following formula:

$$\text{Flow} = k \cdot (Bp - b_0)^L \qquad \text{Formula 1:}$$

where when the bubble point with water at 20° C. is between 0.01 and 0.25 MPa, $k=31026$, $L=-1.00$, and $b_0=0.01034$; and bubble point with water at 20° C. is greater than 0.25 MPa, $k=5797$, $L=-1.35$, and $b_0=0.1379$. In this formula, flow is expressed in L/m2/h, the pressure can be at 1 bar. The embodiment described in this formula is for membranes of thickness in the range of approximately 100-140 micrometers.

For thicker membranes, there is not necessarily a consistent relationship between the thickness and the flow rate. This is because in some embodiments of thicker membranes not all of the thickness plays a role in or contributes to or affects flow rate.

Medical Devices

Embodiments of the invention relate to medical devices containing the matrices. For example, an intravenous (IV) device containing the matrix typically can deploy the matrix in a disc form, enclosed in a compartment having an inlet and an outlet. Tubing of appropriate dimensions and composition is connected to the inlet (upper tubing) and to the outlet (lower tubing). The upper tubing carries fluid from, for example, a 1-liter container to the matrix compartment. Fluid passes through the matrix and continues to pass through the compartment's outlet to the lower tubing. The lower tubing carries the fluid to its point of use; generally the tubing attaches to a needle which delivers the fluid to the venous system of a patient. When the fluid is depleted from the container air flows into and fills the upper tubing; the flow-stop capability of the matrix prevents air from entering the lower tubing.

EXAMPLES

Embodiments of the invention are exemplified and additional embodiments are disclosed in further detail in the following Examples, which are not in any way intended to limit the scope of any aspect of the invention described herein.

Example 1

Method of Making an Asymmetric Membrane Dope Mix

This example demonstrates a method of making a membrane dope mix according to an embodiment of the invention.

Liquids and solids are premixed separately. Solids are then added under agitation. The mixture is continuously stirred and heated for 24 hours to obtain complete solution. The temperature of mixing is usually between 50° C. and 70° C., but can be higher or lower depending upon the composition of the mix, for example, some mixing temperatures can be mixed at 25, 30, 35, 40 or 45 degrees C., and others can be 75, 80, 85, 90 or more degrees C. Upon solution the mixture is filtered then degassed under vacuum for up to 24 hours, or more before use.

Example 2

Effect of Rinse Temperature

This example demonstrates the effects of rinse temperature in embodiments of the invention.

In this example, the following solution was used for the production of the membrane.

TABLE 1

Solution for production of the membrane

| Component | Weight percent |
|---|---|
| Polyethylene Glycol, (PEG 400) | 1~35 |
| Polyethylene Glycol, (PEG 200) | 0~15 |
| Glycerol | 0.1~20 |
| Water | 0.5~10 |
| Polyethersulfone (PES) | 4~25 |
| Dimethyl formamide | 0~45 |
| N-N-methyl pyrrolidone | 10~70 |
| Lithium chloride | 0~1 |
| Caprolactam | 0~20 |
| Polyvinyl pyrrolidone (PVP) k-90 | 2~15 |
| Polyvinyl pyrrolidone (PVP) k-30 | 0~12 |
| Triethylene glycol | 0~5 |

The components were added to the mixing vessel at room temperature and were dispersed mechanically. After 30 minutes, heat was applied so that the system reached a temperature of at least 48° C. Mechanical agitation was continued until the solution is complete.

Solution was applied to a moving belt, such that passed under a doctor of height 0.45 mm.

The wet film passed through a gas chamber containing primarily nitrogen and water vapor, RH of 40% at 30° C., then into water bath at 25° C. and then collect as a wet matrix.

In a subsequent operation the wet matrix was rinsed and dried.

FIG. 1 and Table 2 show the effect of rinsing conditions on the flow performance of resultant dried matrix. A rinse bath of DI water was used, where the wet matrix residence time was 6 minutes, after which it was dried at a temperature of 190° C. Residual PEG in the membrane was determined by extraction.

The data show that rinsing temperature has a significant effect on the flow performance of the matrix.

TABLE 2

Effect of Rinse Bath Temperature of Flow of Matrix

| Matrix Bubble Point [MPa] | Flow relative to Flow at 70° C. rinse bath Bath Temperature [° C.] | | |
|---|---|---|---|
| | 20 | 50 | 70 |
| 0.55 | 5.9 | 2.0 | 1.0 |
| 0.40 | 4.3 | 1.4 | 1.0 |
| 0.20 | 7.3 | 4.0 | 1.0 |
| Av. Residual PEG | 3.1% | 1.1% | 0.3% |

Example 3

Effect of Rinse Temperature Across Bubble Point Range

Figure 2:
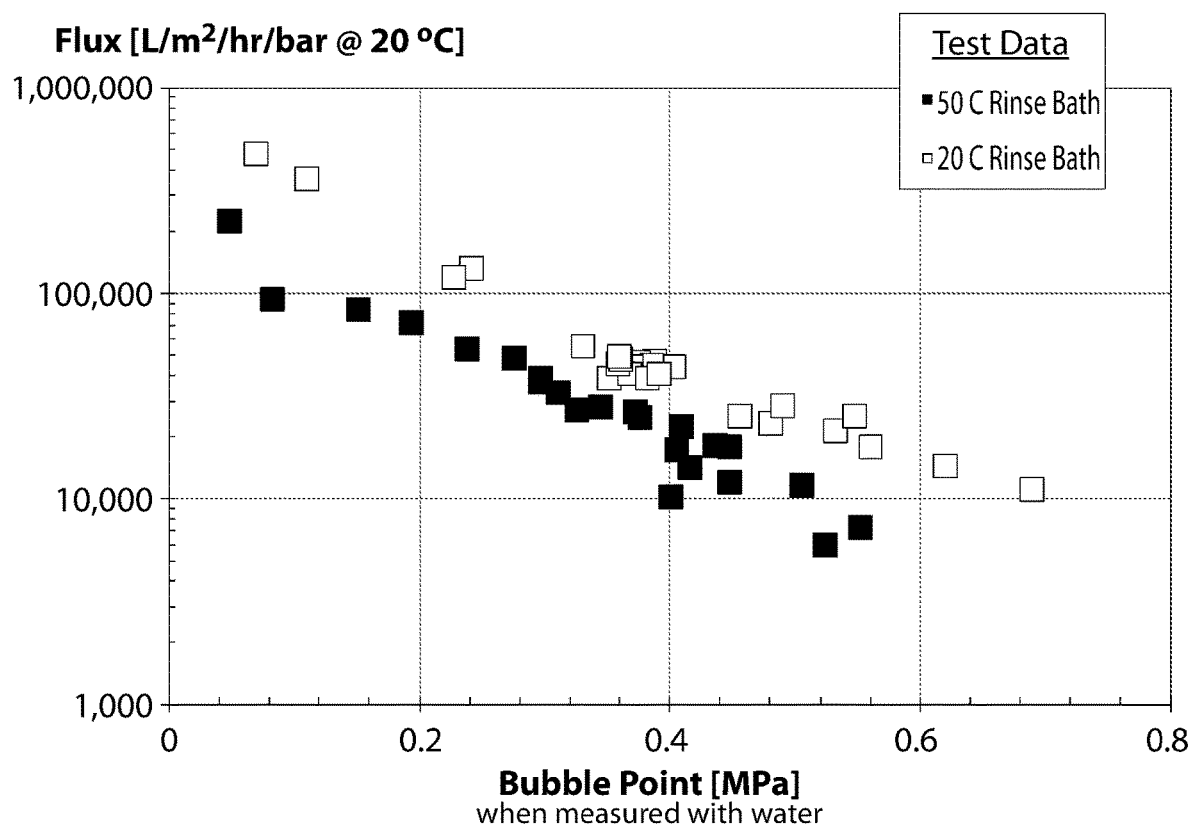
FIG. 2 depicts results from experiments testing the effect of rinse temperature on the matrix.

As per Example 2, matrices of a wide range of bubble points were produced. They were rinsed at either 20° C. or 50° C. FIG. 2 shows the effect rinsing temperature has on the flow of the matrices. The data show that rinsing temperature has a significant effect on the flow performance of the matrix across the range of bubble points.

Example 4

Effect of Second Rinse

This example demonstrates the effect of the second rinse after "curing."

Figure 3:
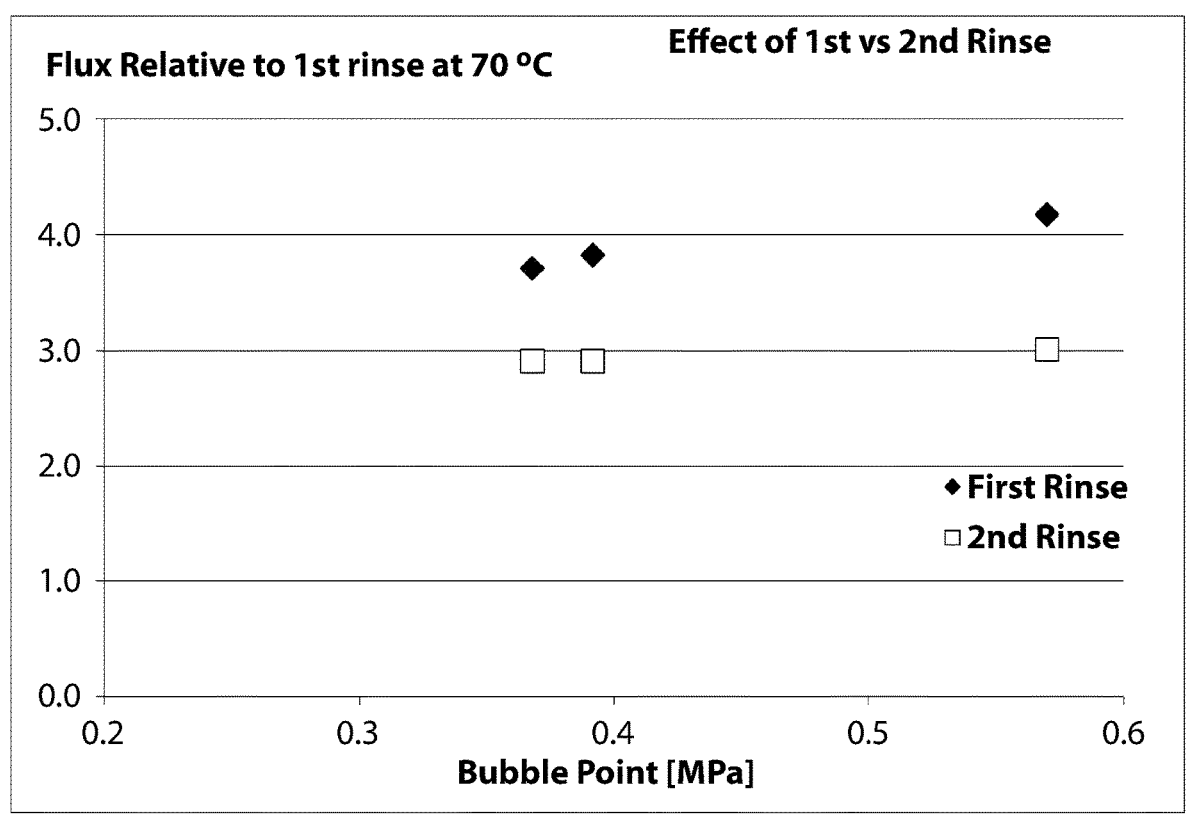
FIG. 3 depicts results from experiments testing the effect of a second rinse on the matrix.

As per Example 2, matrices of a range of bubble points were produced. They were rinsed once at 20° C. for 6 minutes and dried at 190° C. Then rinsed a second time for 15 minutes, with rinse temperature at 65° C., and dried at 180° C. The data in Table 3 and FIG. 3 show that flow performance of the matrix obtained in a first rinse, can be reduced by additional rinsing after the matrix have been dried.

TABLE 3

Effect of a 2nd Rinse on Flow of Matrix

| Matrix Bubble Point [MPa] | Flow relative to Flow at 70° C. rinse bath one time rinse | |
|---|---|---|
| | 1st Rinse | 2nd Rinse |
| 0.57 | 4.2 | 3.0 |
| 0.39 | 3.8 | 2.9 |
| 0.37 | 3.7 | 2.9 |

Example 5

Effect of Drying Temperature

Figure 4:
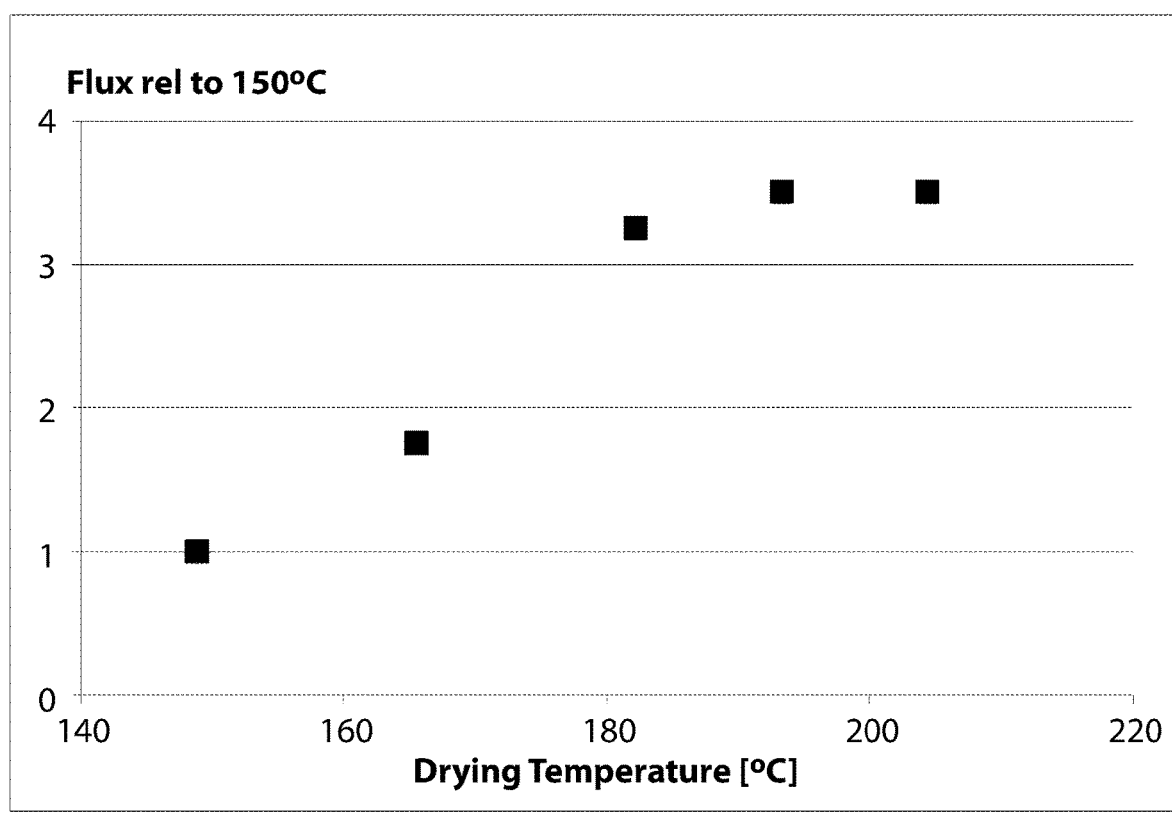
FIG. 4 depicts results from experiments testing the effect of drying temperature on the matrix.

As per Example 2, matrices of a bubble point of 0.5 MPa were produced. They were rinsed once at 20° C. for 6 minutes and then dried at the temperatures shown in Table 4. The data in FIG. 4 shows that flow performance of the matrix is strongly drying-temperature-dependent, to a critical temperature and then insensitive to increases beyond that.

TABLE 4

Effect of a Drying Temperature on Flow of Matrix

| Drying Temperature [° C.] | Flow relative to Flow of Membrane dried at 150° C. |
| --- | --- |
| 150 | 1.0 |
| 165 | 1.8 |
| 180 | 3.3 |
| 190 | 3.5 |
| 205 | 3.5 |

Example 6

Flow Rate Compared to Market

Figure 5:
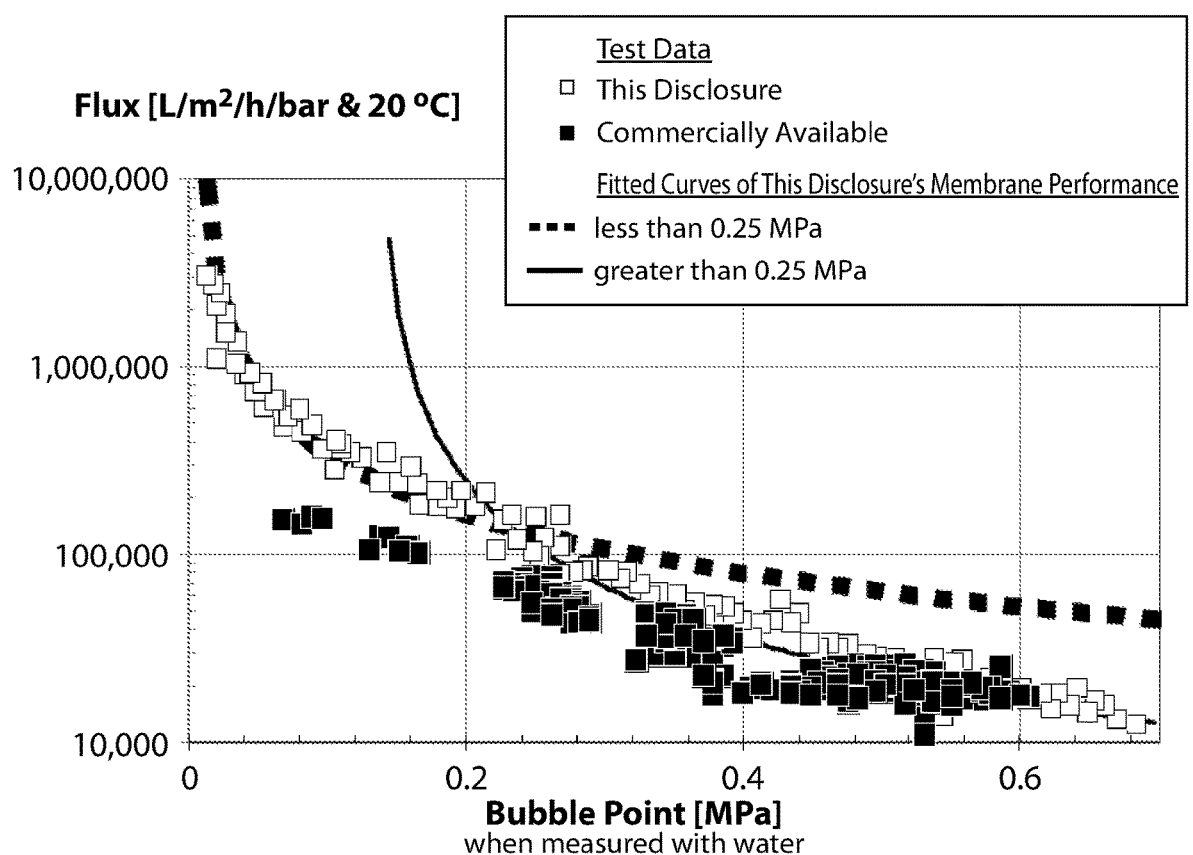
FIG. 5 depicts results from experiments measuring the flow rate of the matrix compared to market available membranes.
Figure 6:
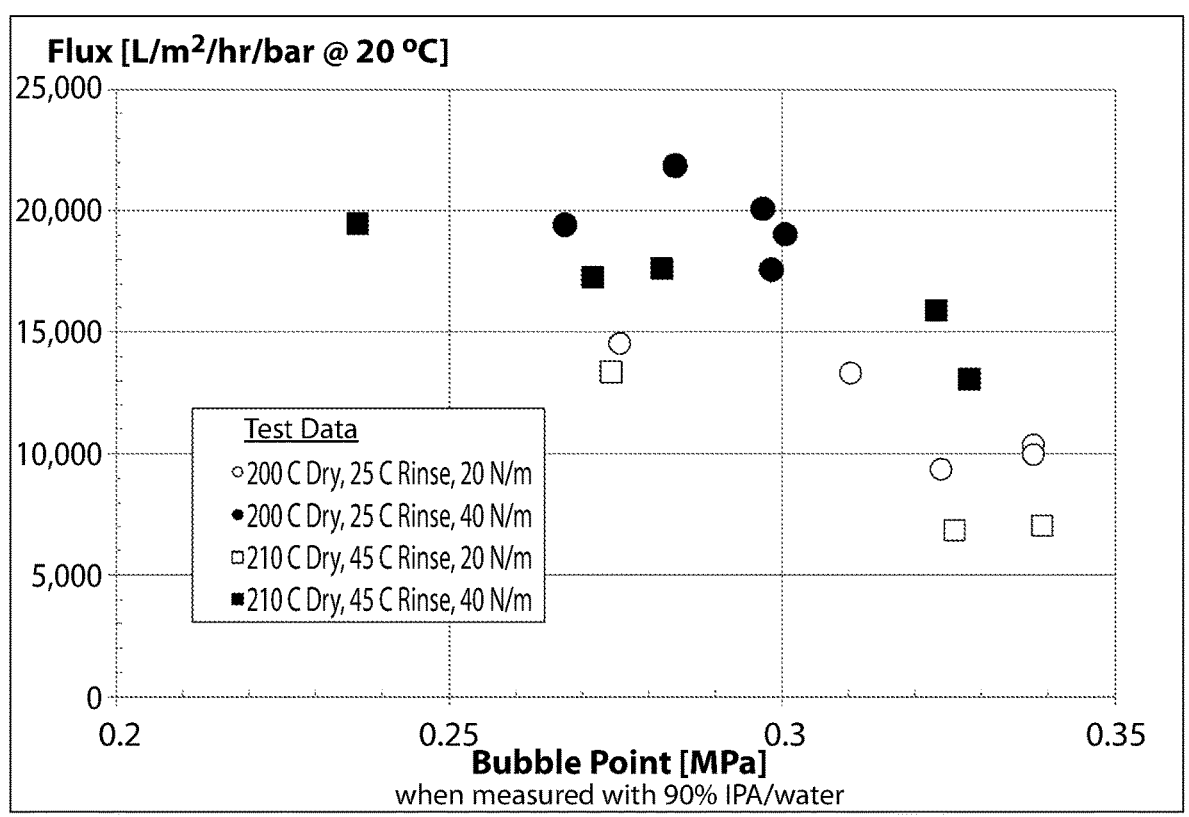
FIG. 6 depicts results from experiments measuring the effect of tension during drying.
Figure 7A:
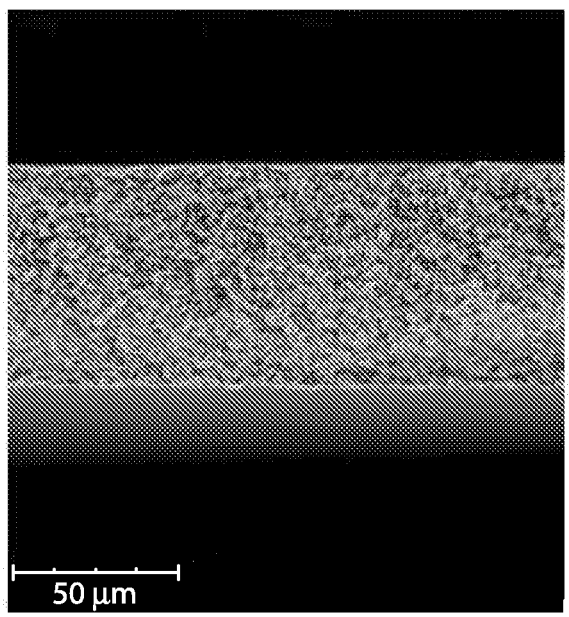
FIG. 7 depicts scanning electron microscope (SEM) images of the matrix compared to market available membranes.
Figure 7A:
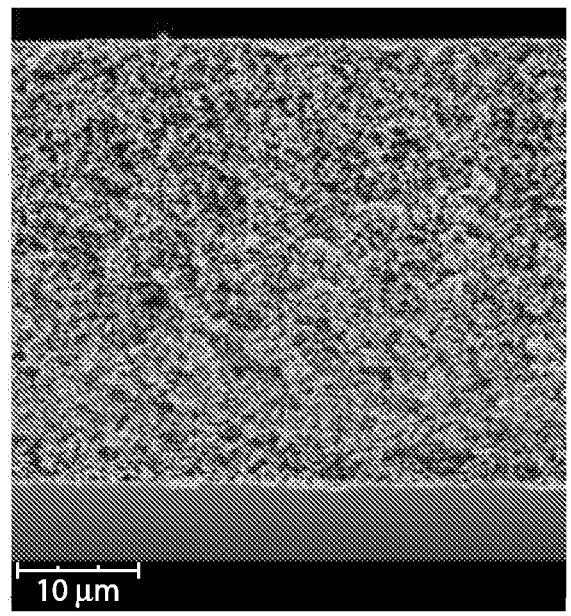
Figure 7B:
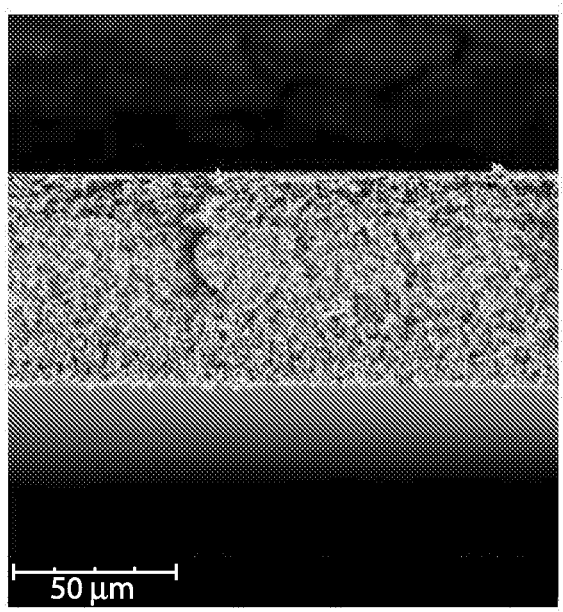
Figure 7B:
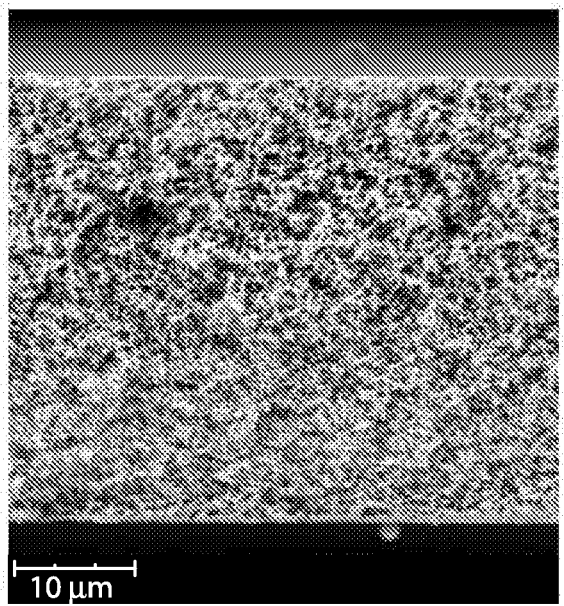
Figure 7C:
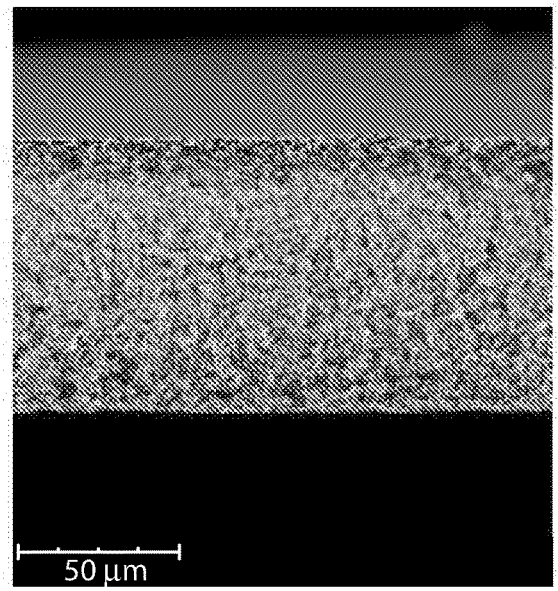
Figure 7C:
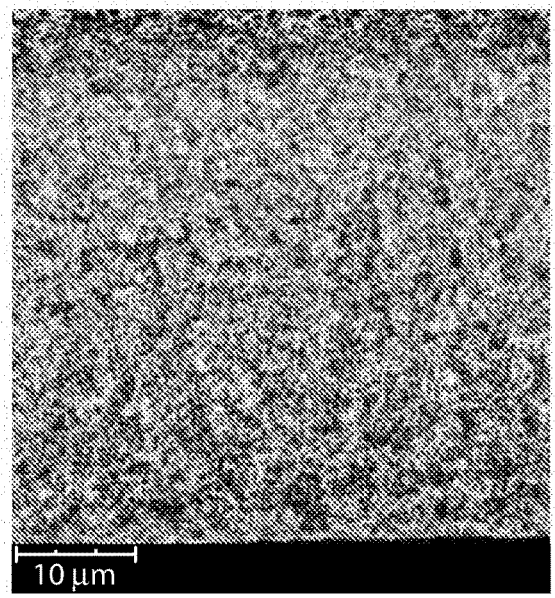
Figure 7D:
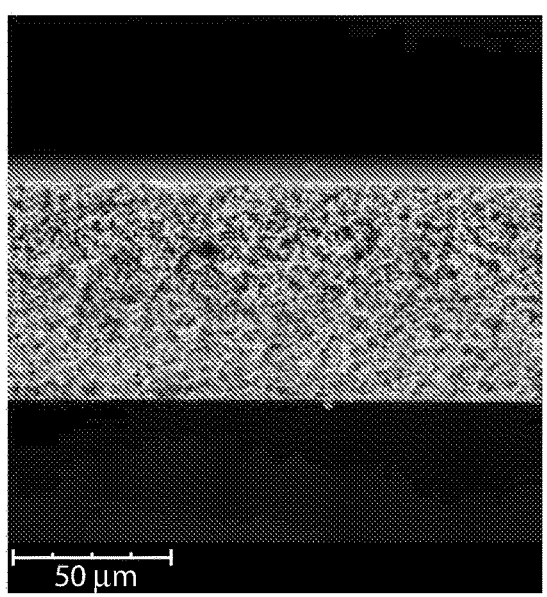
Figure 7D:
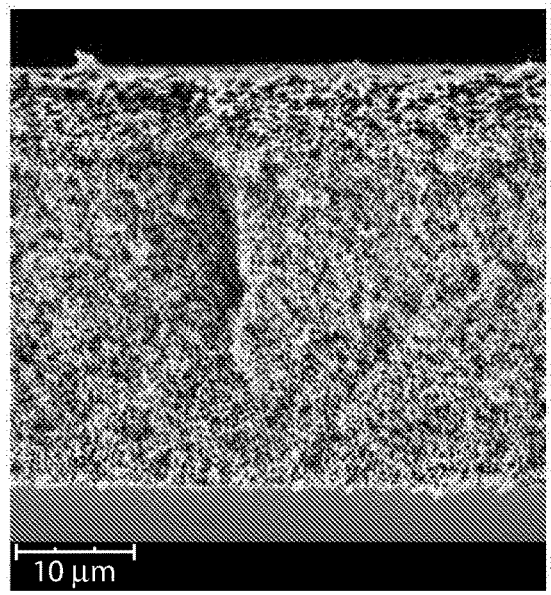

Flow rates of commercially available membranes were tested along with their bubble points. As per Example 2, matrices of a varying bubble points were produced and their flow rates measured. FIG. 5 shows the data of this testing along with data from matrices of this disclosure. Matrices made per this disclosure have flow rates which are on average larger than the commercially available membranes measured for any given bubble point. Formula 1 described above can refer to the flow rates of the matrices made per this disclosure.

Example 7

Example Drying Under Tension

As per Example 2, matrices of varying bubble points of were produced. They were rinsed for 6 minutes and then dried at the temperatures shown in FIG. 3. During the drying process, the matrices were held with longitudinal tension as shown. The data show that flow performance of the matrix is strongly dependent upon the tension applied during drying, with increasing tension improving the flow performance.

Example 8

Example Matrix and Properties

FIG. 7 shows SEM images of embodiments of the invention compared to commercially available membranes. 0.1 μm commercial membrane, 0.2 μm commercial membrane, 0.6 MPa bubble point membrane of the invention, and 0.4 MPa bubble point membrane of the invention.

Example 9

Process of Making Membrane

Figure 8:
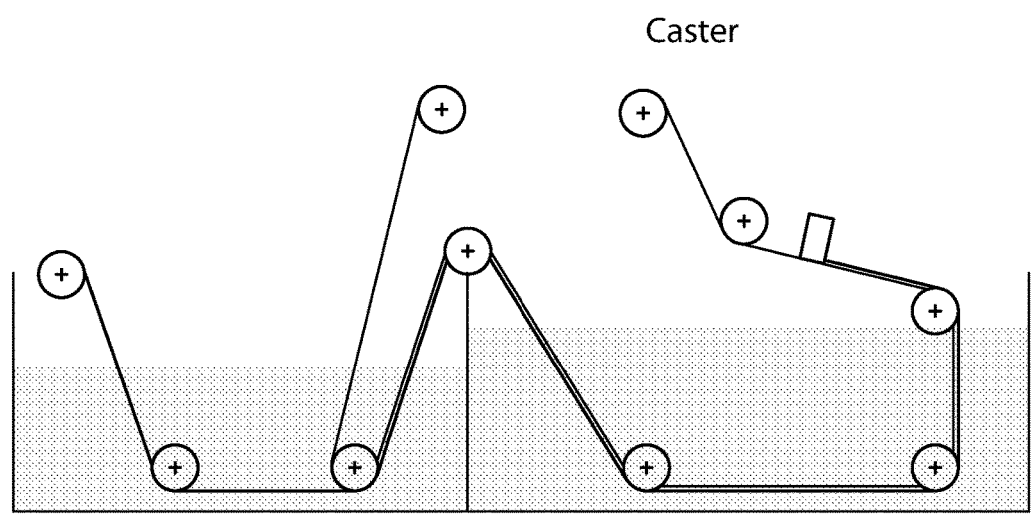
FIG. 8 depicts an embodiment of the system for making the membrane.
Figure 8:
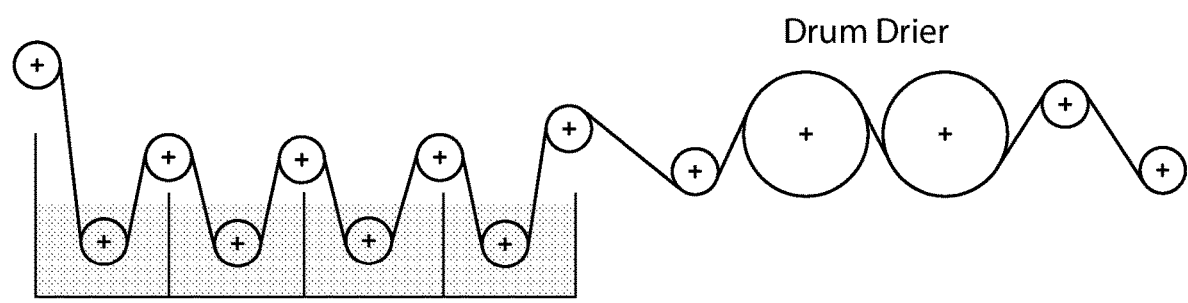

FIG. 8 shows an example embodiment of the system for making the membrane. The system is for continuous production of flat sheet material, where the casting solution is brought to a moving carrier through an applicator—such as a three sided box with a doctor blade. The applied solution layer is carried by the moving carrier through an open region before entering the coagulation bath through which it then passes. It is carried to a second tank where the nascent matrix is washed for a first time. This nascent matrix is then passed through a second rinse system—here depicted as a second unit operation but this can also be in line and subsequent to the first rinse. The rinsed matrix then passes out of the rinse into a dryer, here depicted as 2 drums in series, but could also be flotation type air dryer or non-contact IR dryers or a combinations of any or all of the above. Upon exiting the dryer the membrane is wound up on a core.

Example 10

PVDF Microporous Membrane

This example demonstrates the effects of drying time on flow rate in an embodiments of the invention.

In this example, the following solution was used for the production of the membrane.

This example demonstrates the effects of rinse temperature in an embodiments of the invention.

In this example, the following formulation was used for the production of the membrane:

| Component | Wt % |
| --- | --- |
| Kynar 761 | 15.6% |
| Sokolan K30 | 4.6% |
| Sokolan K90 | 3.1% |
| NMP | 56.3% |
| IPA | 9.1% |
| TWEEN 80 | 0.9% |
| PEG 400 | 10.0% |
| Water | 0.3% |

The components were mixed under heat until dissolved. Once dissolved, the solution was allowed to equilibrate to room temperature. The solution was cast using a doctor knife on a moving carrier for PE non-woven, gap 0.5 mm, then quenched in a water bath and rinsed for 90 minutes. The matrix was dried under tension until dry.

In a subsequent operation the wet matrix was rinsed and dried.

The membranes were tested and the results were as follows:

| Drying Temperature ° C. | IPA Bubble Point MPa | Water Flow Rate L/m$^2$/h@ 1 bar |
| --- | --- | --- |
| 150 | 0.16 | 21600 |
| 170 | 0.16 | 28800 |
| 250 | 0.16 | 43200 |

Example 11

Effect of Ratio of Polymer in Formulation

Figure 9:
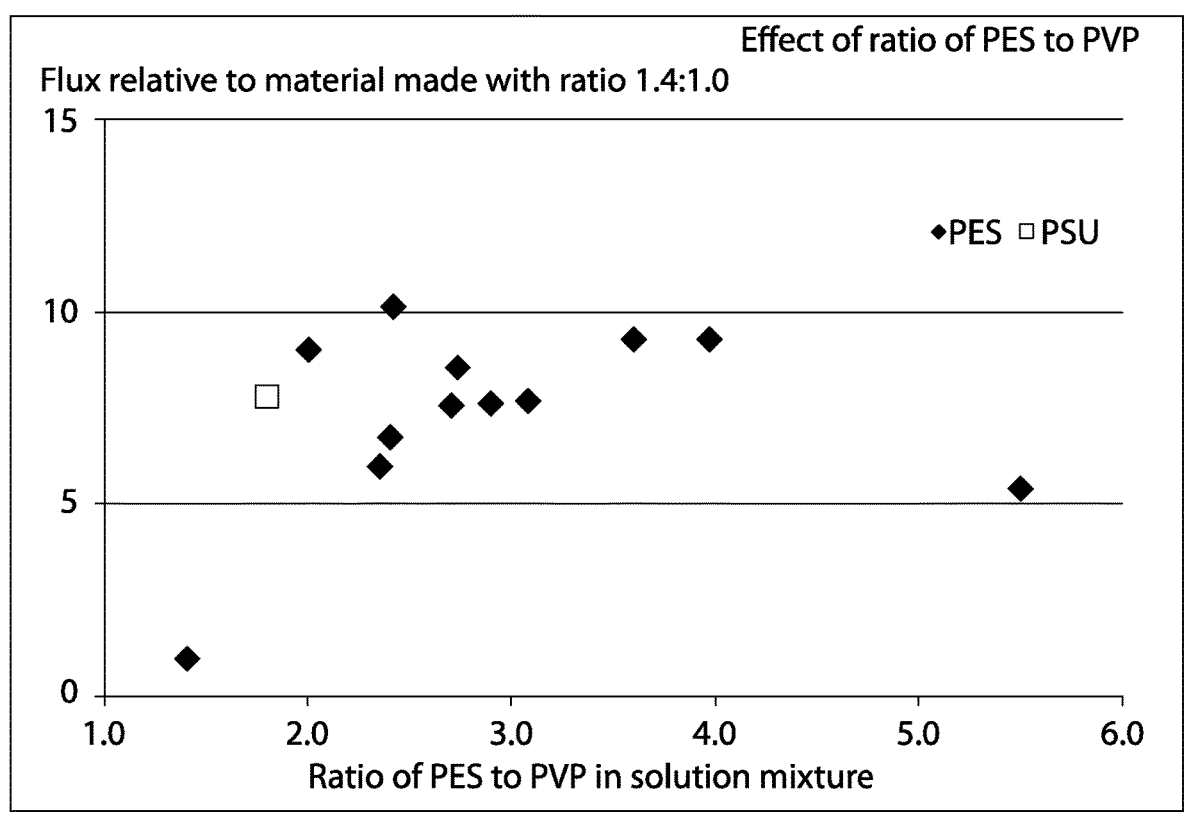
FIG. 9 depicts results of experiments related to the ratio of polymer.

As per Example 2, matrices of a range of bubble points were produced. The ratio of PES to PVP k-90 in the solution mix was varied, holding all other ratios the same. Subsequent processing of each formulation was the same. FIG. 9 shows the ratio of water flow of the resultant membrane to that with a ratio of PES to PVP of 3.6:1.0, at the equivalent bubble point. The resultant membrane bubble points were in the range 20 to 40 psi when measured with 70% IPA in water. Polysulfone (PSU) was substituted for PES in one trial, as noted.

Example 12

Ratio of Glycols in Formulation

Figure 10:
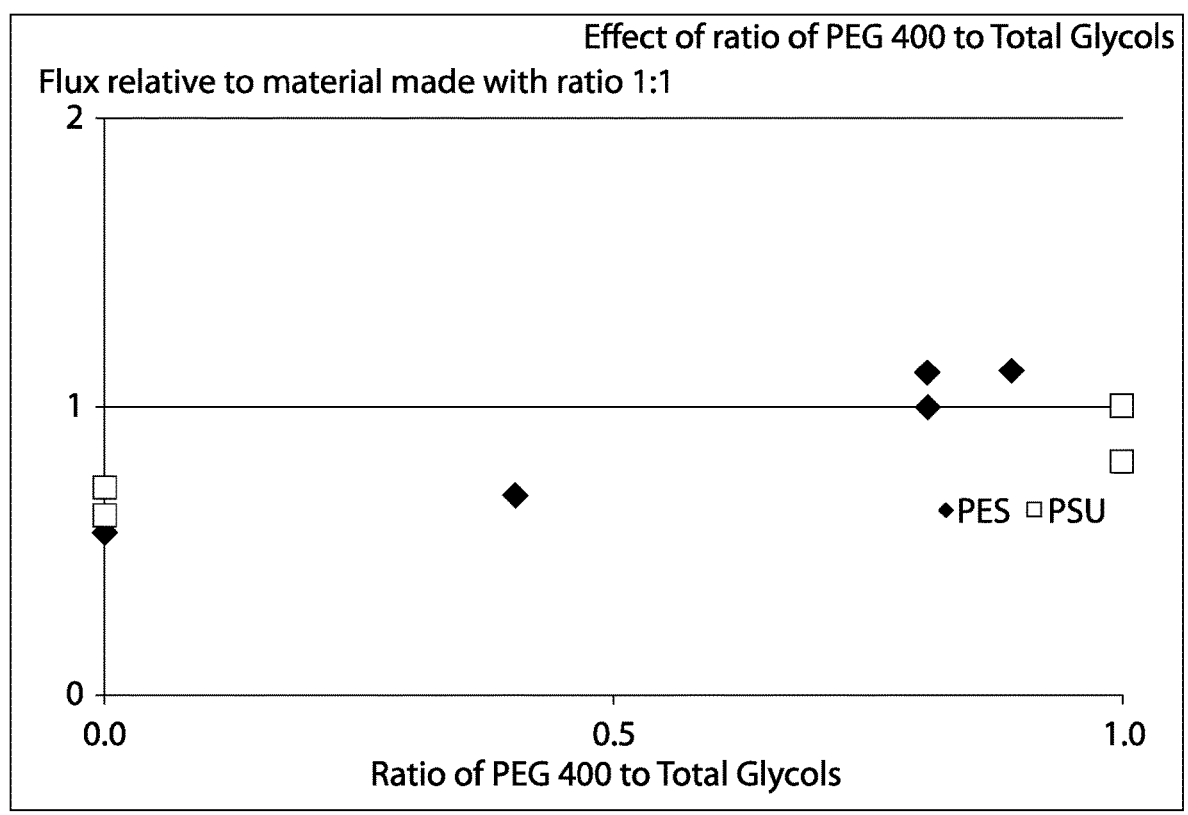
FIG. 10 depicts results of experiments related to the glycols of polymer.

As per Example 2, matrices of a range of bubble points were produced. The ratio of Glycols (weight of PEG 400 relative to total Glycol content) in the solution mix was varied, holding all other ratios the same. Subsequent processing of each formulation was the same. FIG. 10 shows the ratio of water flow of the resultant membrane to that with a ratio of PEG 200 to PEG 400 of 1:1, at the equivalent bubble point. The resultant membrane bubble points were in the range 20 to 40 psi when measured with 70% IPA in water. Polysulfone (PSU) was substituted for PES in several trials, as noted.

It will be apparent to one skilled in the art that varying substitutions and modifications can be made to the invention disclosed herein without departing from the scope and spirit of the invention.

Those skilled in the art recognize that the aspects and embodiments of the invention set forth herein can be practiced separate from each other or in conjunction with each other. Therefore, combinations of separate embodiments are within the scope of the invention as disclosed herein.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A matrix capable of passage of water therethrough having a flow rate at 20° C. that, when tested using the matrix having a thickness of 100-140 micrometers under atmospheric pressure of 1 bar, meets or exceeds a flow value produced by application of Formula 1

$$\text{Flow}=k \cdot (Bp-b_0)^L \qquad \text{Formula 1:}$$

wherein Bp is a bubble point; wherein when the bubble point with water at 20° C. is between above 0.01034 and 0.25 MPa, k=31026, L=−1.00, and $b_0$=0.01034; and when bubble point with water at 20° C. is greater than 0.25 MPa, k=5797, L=−1.35, and $b_0$=0.1379, wherein the flow is expressed in L/m²/h.

2. The matrix of claim 1, having a flow-stop capacity defined by a drop distance of a vertical column of fluid below the matrix and attached thereto, and wherein the matrix possesses a flow-stop capacity at a drop distance of at least 1.5 meter.

3. The matrix of claim 1, wherein the matrix is capable of passage of water therethrough at a rate of at least 140 ml/minute through a matrix area of 0.785 cm².

4. The matrix of claim 1, having a composition comprising at least one substantially non-sulfonated polymer and a compatible polymer, wherein the compatible polymer is compatible with the substantially non-sulfonated polymer.

5. The matrix of claim 4, wherein the compatible polymer comprises a sulfone polymer.

6. The matrix of claim 5, wherein the sulfone polymer comprises polyethersulfone (PES).

7. The matrix of claim 4, wherein the substantially non-sulfonated polymer comprises polyvinylpyrrolidone (PVP).

8. The matrix of claim 7, wherein the PVP has a molecular weight less than 2800 kDa.

9. The matrix of claim 7, wherein the PVP has a molecular weight between 3 kDa and 2800 kDa.

10. The matrix of claim 1, wherein the matrix is capable of passage of water therethrough at a rate of at least 120 ml/minute through a matrix area of 0.785 cm², and further having a flow-stop capacity defined by a drop distance of a vertical column of fluid below the matrix and attached thereto, and wherein the matrix possesses a flow-stop capacity at a drop distance of at least 1 meter.

* * * * *